United States Patent
Hok et al.

(10) Patent No.: US 9,746,454 B2
(45) Date of Patent: Aug. 29, 2017

(54) MULTIFUNCTIONAL BREATH ANALYZER

(75) Inventors: Bertil Hok, Vasteras (SE); Lars Tenerz, Vasteras (SE); Leif Smith, Vasteras (SE); Annika Kaisdotter Andersson, Vasteras (SE)

(73) Assignee: HOK INSTRUMENT AB, Vasteras (SE)

( * ) Notice: Subject to any disclaimer, the term of this patent is extended or adjusted under 35 U.S.C. 154(b) by 276 days.

(21) Appl. No.: 13/884,359

(22) PCT Filed: Oct. 6, 2011

(86) PCT No.: PCT/SE2011/051196
§ 371 (c)(1),
(2), (4) Date: May 9, 2013

(87) PCT Pub. No.: WO2012/064252
PCT Pub. Date: May 18, 2012

(65) Prior Publication Data
US 2013/0231871 A1     Sep. 5, 2013

(30) Foreign Application Priority Data

Nov. 9, 2010 (SE) ..................................... 1051175

(51) Int. Cl.
*G01N 33/497* (2006.01)
*A61B 5/087* (2006.01)
(Continued)

(52) U.S. Cl.
CPC ........... *G01N 33/497* (2013.01); *A61B 5/087* (2013.01); *A61B 5/4845* (2013.01);
(Continued)

(58) Field of Classification Search
CPC .................................................. G01N 33/427
(Continued)

(56) References Cited

U.S. PATENT DOCUMENTS 5,874,737 A * 2/1999 Bytyn ................ G01N 21/3504
250/338.5
7,279,132 B2   10/2007 Sultan et al.
(Continued)

FOREIGN PATENT DOCUMENTS

CN    101292158 A    10/2008
CN    101631497 A     1/2010
(Continued)

OTHER PUBLICATIONS

International Search Report dated Feb. 22, 2012, corresponding to PCT/SE2011/051196.
(Continued)

*Primary Examiner* — Lisa Caputo
*Assistant Examiner* — Tarun Sinha
(74) *Attorney, Agent, or Firm* — Young & Thompson

(57) ABSTRACT

A multifunctional breath analyzer includes a receptor unit for receiving a breath sample from a test subject, a sensing unit providing a signal corresponding to the concentration of at least one volatile substance within the sample, elements for providing a signal indicative of the dilution of the breath sample, and an analyzing unit/processing unit for the identification and quantification of the volatile substance of the breath sample. The signal processing unit is configured to perform at least two different calculations for the quantification, and the signal processing unit is also configured to automatically display the result of a selected calculation, the selection being based on the signal indicating dilution.

20 Claims, 4 Drawing Sheets

(51) Int. Cl.
*A61B 5/00* (2006.01)
*G01N 21/3504* (2014.01)
*A61B 5/083* (2006.01)
*G01N 21/03* (2006.01)

(52) U.S. Cl.
CPC ....... *A61B 5/6885* (2013.01); *G01N 21/3504* (2013.01); *G01N 33/4972* (2013.01); *A61B 5/0836* (2013.01); *G01N 21/031* (2013.01)

(58) Field of Classification Search
USPC .............................................. 702/19; 73/23.3
See application file for complete search history.

(56) References Cited

U.S. PATENT DOCUMENTS

| | | | |
|---|---|---|---|
| 2003/0228702 A1* | 12/2003 | Stock .................... | A61B 5/097 436/132 |
| 2004/0149579 A1* | 8/2004 | Palmer et al. ................ | 204/431 |
| 2008/0038207 A1 | 2/2008 | Edwards et al. | |
| 2008/0056946 A1* | 3/2008 | Ahmad ................. | A61B 5/097 422/68.1 |
| 2008/0061238 A1* | 3/2008 | Hok .................... | G01N 33/497 250/340 |
| 2009/0087920 A1 | 4/2009 | Pettersson et al. | |
| 2009/0178491 A1* | 7/2009 | McKitterick ........... | G01W 1/00 73/861.47 |
| 2010/0051029 A1* | 3/2010 | Jafari ................ | A61M 16/0858 128/204.23 |
| 2010/0063409 A1 | 3/2010 | Hok | |
| 2010/0268425 A1* | 10/2010 | Pettersson ............ | B60K 28/063 701/45 |

FOREIGN PATENT DOCUMENTS

| | | |
|---|---|---|
| EP | 0327396 A2 | 8/1989 |
| EP | 1688741 | 8/2006 |
| WO | 98/20346 | 5/1998 |
| WO | 2008/108714 | 9/2008 |
| WO | 2010093317 A1 | 8/2010 |

OTHER PUBLICATIONS

Chinese Office Action, dated Jan. 15, 2014, from corresponding CN application.
European Search Report, dated Nov. 21, 2016, from corresponding EP application No. 11839384.2.

* cited by examiner

MULTIFUNCTIONAL BREATH ANALYZER

TECHNICAL FIELD

The invention relates to the analysis of breath (exhalation air) from a test subject. The analysis comprises the identification and quantification of one or several volatile substances, e.g. ethanol, methanol, acetone, carbon monoxide, carbon dioxide, ammonia, nitric oxides. It may have medical, social, security, or judicial purposes, depending on the situation, and the substances involved. The situation may call for different requirements with respect to measuring accuracy, specificity, speed of response, etc. In particular the invention relates to an apparatus for such analysis.

BACKGROUND

Breath analyzers according to the state of the art are designed for specific situations and application areas. A variety of products exists for applications in screening, clinical diagnostics, and for evidential purposes for the determination of breath alcohol concentration. For the latter category, high priority requirements are measuring accuracy and specificity. For screening purposes, speed of response and simplicity for the test person are more important, especially when the fraction of positive response, i e concentration exceeding a certain threshold value, is expected to be small. This is the case in testing of sobriety of vehicle drivers, including alcolocks or similar devices.

In evidential instruments and qualified diagnostic instruments, infrared spectroscopy is being used as the measuring principle, resulting in very high accuracy and specificity. For screening purposes, simpler sensors based on catalysis, e.g. fuel cell or semiconductor elements, are being used. They are advantageous with respect to production cost, but have drawbacks when it comes to reliability. The catalytic function is difficult to control, and the sensors have limited life time. In most breath analyzers the test subject is required to deliver forced expiration into a tight-fitting mouthpiece. The procedure is time consuming and problematic to persons with impaired respiratory function.

SUMMARY OF THE INVENTION

The present invention is concerned with a multifunctional breath analyzer which simultaneously fulfills the seemingly conflicting requirements mentioned above within one single enclosure. The breath analyzer according to the invention can be used for a number of different purposes that have hitherto called for different pieces of equipment. Thereby increased flexibility is obtained, along with reduced time consumption, and lower cost for the user. Both screening and more demanding tasks may be carried out with one and the same piece of equipment.

In the breath analyzer according to the invention, screening may be performed without physical contact between the breath analyzer and the test subject, with the benefits of easy and fast operation, and requiring a minimum effort of the test subject. However, it also means that the breath sample is being diluted with ambient air. By measuring the concentration of a tracer substance, e.g. carbon dioxide ($CO_2$), within the sample, the degree of dilution may be estimated, allowing an estimation of the true breath concentration.

According to the invention the breath analyzer comprises a receptor unit for receiving a breath sample from a test subject, a sensing unit providing a signal corresponding to the concentration of at least one volatile substance within the sample, means for providing a signal indicative of the dilution of the breath sample, and an analyzing unit/processing unit for the identification and quantification of the volatile substance of the breath sample. The signal processing unit is configured to perform at least two different calculations for the quantification, and the signal processing unit is also configured to automatically display the result of a selected calculation, the selection being based on the signal indicating dilution.

The means for indicating dilution may either comprise a sensor responsive of the tracer substance or one responsive of the tightness of connection between the respiratory organs of the test subject and the sensing unit.

The device according to the invention is defined in claim 1.

In a preferred embodiment, the breath analyzer according to the invention comprises an autonomous, handheld unit which is simple to use independently of the position, posture and condition of the test person.

In another preferred embodiment the breath analyzer can be installed and embedded in the instrumentation at the driver's position of a vehicle. In the screening mode of operation, no active participation of the driver is required. However, if the estimated substance concentration exceeds a certain threshold, the driver may be urged to provide a second breath test using a tight-fitting mouthpiece connected to the same breath analyzer.

The present invention is defined in the appended claims, and a more detailed description is provided below, in relation to the enclosed drawings, wherein FIG. 1 schematically shows the building blocks of the breath analyzer according to the invention;

DETAILED DESCRIPTION

Figure 1:
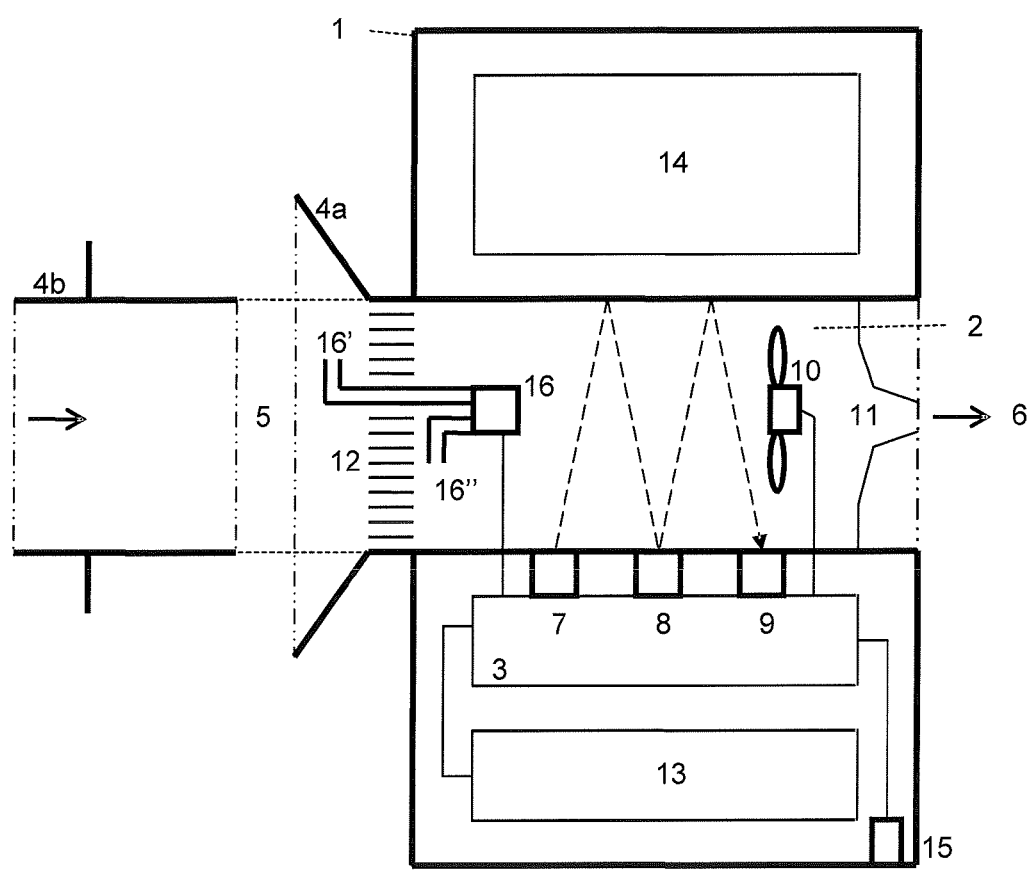

FIG. 1 shows the building blocks of a preferred embodiment of the breath analyzer according to the invention. The analyzer is physically built into an enclosure 1, designed for handheld use. Its outer physical dimensions are modest, typically 150×50×30 mm. To obtain the necessary durability it needs to be resistant to environmental stress of various kinds, including extreme temperature, humidity, pressure, shock, vibration, and electromagnetic interference. In particular, the enclosure 1 comprises a structured metallic material, or a shock resistant polymer in order to fulfill its functional requirements.

The enclosure 1 includes a sensing unit 2 coupled to a signal processing unit 3. The sensing unit 1 is equipped with an inlet 5 and an outlet 6 allowing the breath sample to be passed through it with or without the assistance of a fan 10. The fan 10 may also supply a bias flow to assist the breath flow during measurement, and improve sensitivity of highly diluted samples. Preferably, a flap valve 11 at the outlet 6 secures that the flow is unidirectional. The volume of the sensing unit 2 is typically less than 100 ml.

The breath sample is fed into the inlet 5 of the sensing unit 2 via a receptor 4a, which in FIG. 1 is shown mechanically secured to the inlet 5 of the sensing unit 2. When the receptor 4a is used for contactless reception of a breath sample at a distance of a few centimeters from the mouth and nose of the test person, it preferably has the shape of a scoop, mug, cup or funnel, which may be detachably secured to the enclosure 1.

Another shape preferred for undiluted breath sampling, which is shown separately in FIG. 1, is tubular 4b with or without a flange to ensure tight connection between the sensing unit 2 and the test subject's lips and therefore also the respiratory organs. A tight connection may also be accomplished if the receptor has the shape of a face mask enclosing both the mouth and nose of the test subject.

A particle filter 12 consisting of a porous and permeable substance, typically a fibrous polymer, is preferably included in the sensing unit 2 or receptor 4a, b with two distinctive purposes. First it separates liquid droplets and solid particles that may accompany expired air from the volatile substances of main interest, thereby avoiding contamination of sensitive surfaces within the sensing unit 2.

The second purpose of the filter 12 is to define, together with the pressure sensor 16, means for providing a signal indicative of the tightness of connection between the respiratory organs of the test subject and the sensing unit 2. Tightness is one indication of an undiluted breath sample. The filter 12 exhibits a small but well-defined flow resistance. The flow through the filter 12 is preferably nearly laminar, resulting in a linear or polynomial relationship between the flow and the differential pressure across the up- and downstream ends of the filter 12. The differential pressure sensor 16 is included for the purpose of responding to this pressure. At the onset of a breath sample, the pressure peak corresponds to the respiratory driving force of the test subject, and is indicative of a tight connection between the sensing unit 2 and the subject's respiratory organs. The input openings 16', 16" of the pressure sensor 16 are preferably directed perpendicular to the main flow direction in order to minimize the influence of dynamic pressure built up according to the basic theory of Bernoulli.

An alternative embodiment of means for providing a signal indicative of tightening makes use of other gas flow sensing devices, e.g. based on hot-wire anemometry, vortex shedding, ultrasonic transit time measurement, or Doppler frequency shift. Necessary prerequisite are response time of 0.1 second or less, and immunity to environmental variations.

Preferably, the sensing unit 2 includes sensor elements 8, 9 responsive both to the substance of interest 9, and a tracer substance 8, e.g. $CO_2$ or water vapor. Indication of an undiluted breath sample is provided by the latter element 8. If the $CO_2$ concentration exceeds a certain value, e.g. coinciding with the normal alveolar concentration, the sample may be considered undiluted.

In a first embodiment of the sensing unit 2, it includes a source 7 of electromagnetic radiation within the infrared (IR) wavelength range, and IR detectors 8, 9 equipped with band pass type interference filters tuned to wavelength intervals which coincide with absorption peaks of the substances to be determined. For ethanol and $CO_2$ 9.5±0.3 μm (1 μm=$10^{-6}$ m) and 4.26±0.05 μm, respectively, are suitable wavelength intervals. Other substances have other preferred wavelength intervals.

It is schematically indicated in FIG. 1 that the detectors 8, 9 are reached by the IR beam emitted by the source 7 after reflections against the inner wall of the measuring volume which is preferably covered by a thin film of gold or aluminum, or other highly reflecting material, and having appropriate shapes to collimate the beam. The IR beam is reflected once before reaching the detector 8, and reflected three times before reaching the detector 9. Thus the optical path is much longer for the detector 9, resulting in a higher sensitivity to absorption. Therefore, detector 9 is used for detecting the volatile substance of primary interest, whereas the detector 8 is used for the tracer substance. Moreover, it is desired to optimize the optical path and aperture to the expected concentration of the substance to be analyzed in accordance with principles described by J. U. White (J. Opt. Soc. Amer., vol 32, 1942, pp 285-289).

The IR source 7 is preferably generating repetitive pulses of IR radiation with a repetition frequency of 5-100 Hz, which determines the time resolution of the analyzer. The IR source 7 preferably includes a black body radiating thin membrane in order to allow high repetition frequency. The IR detectors 8, 9 are preferably thermopiles in order to provide maximum signal to noise ratio, and consequently maximum sensitivity and resolution.

In a second embodiment of the sensing unit 2, a catalytic sensor including an electrochemical cell or a semiconductor element is being used for identifying and quantifying the volatile substance of interest, and the tracer substance.

The signal processing unit 3 preferably includes integrated analog and digital circuit elements for signal processing and control. Preferably one or several microprocessors are included for signal processing, management of signals to a display 14 for indication of measurement results, and for data communication with external equipment, e.g. a personal computer or other peripheral equipment connectable by a dedicated connector 15.

In a preferred embodiment, the breath analyzer according to the invention is operating as an autonomous, handheld unit. Power supply is provided by a battery 13 which is preferably rechargeable via a mains adapter. In another preferred embodiment, the breath analyzer is embedded into an instrument panel, and used together with other equipment.

As already mentioned, estimation of the dilution of the breath sample is performed by the use of a tracer substance, e.g. $CO_2$. The partial pressure of $CO_2$ within deep (alveolar) breath air is typically 4.8 kPa, corresponding to 4.8% by volume, whereas the background ambient concentration seldom exceeds 0.1% v/v. The degree of dilution therefore can be calculated from the ratio $CO_{2alv}/SO_{2meas}$, where $CO_{2alv}$ and $CO_{2meas}$ are the alveolar and measured concentrations, respectively. The variability of $CO_{2alv}$ between different individuals expressed as one standard deviation is relatively modest, of the order of 10% of the average.

In the present invention, the measured concentration of a substance in a diluted sample is multiplied by $CO_{2alv}/CO_{2meas}$ in order to obtain an estimated value of the undiluted concentration. This mode of operation is extremely rapid and convenient for the test person, but exhibits a relatively large error due to the variability of $CO_{2alv}$. Water vapor can be used as an alternative tracer substance, however with the addition of careful determination of the background concentration which at unfavorable conditions may nearly coincide with the signal.

Transfer from a screening mode of operation into one of higher measuring accuracy is accomplished in the present invention by identifying an undiluted breath either by the sensor element 8 responsive of the tracer substance, or by means of a signal indicative of a tight-fitting connection between the respiratory organ and the sensing unit of the breath analyzer. This signal is provided by the pressure sensor 16.

In the absence of a signal indicating an undiluted sample, an estimation of the sample dilution is used in the calculation of the substance concentration. In the presence of such a signal the estimation of dilution may be omitted, resulting in higher accuracy. Thus the dilution signal is enabling the breath analyzer to be automatically switching between screening operational modes and those of high accuracy.

Figure 2:
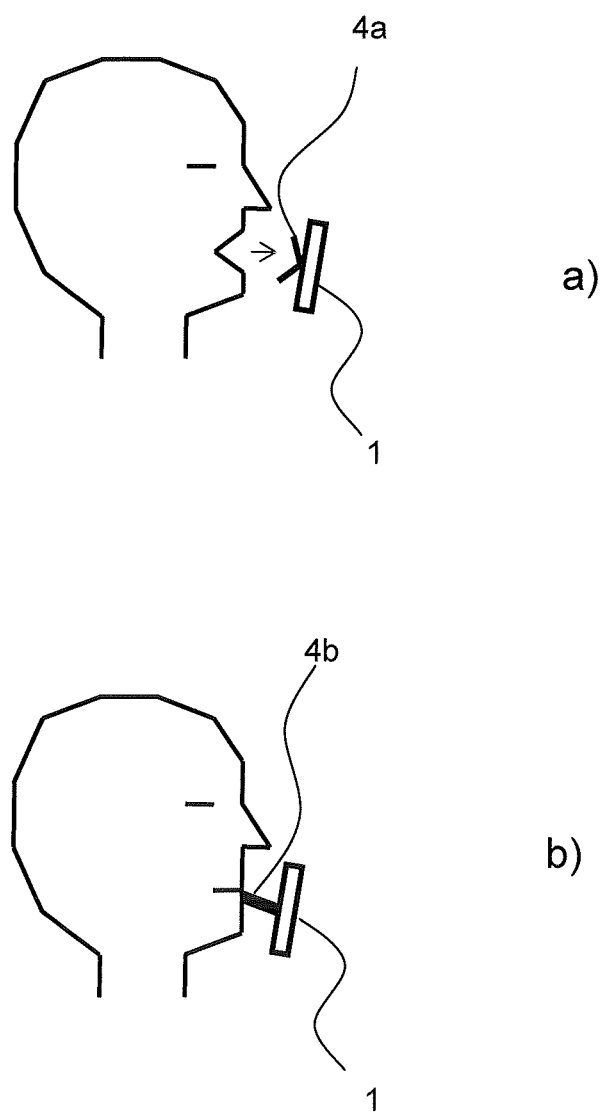
FIG. 2 illustrates examples of use.

FIG. 2 schematically shows two operating modes, or functionalities, of the breath analyzer according to the invention. In FIG. 2 a) contactless measurement is being performed with the enclosure 1 handheld at a distance of a few centimeters from the test person. By the funnel-shaped receptor 4, expiratory air flow is being captured, however with some dilution of ambient air. By the previously described ratioing procedure or algorithm, the concentration of the substance of primary interest can be corrected taking the dilution into account, providing an estimated value of its actual breath concentration. The determination according to FIG. 2 a) can be performed in a few seconds, and by forced ventilation of the measuring volume, the apparatus is rapidly ready for a new test, without the need to physically replace any items. FIG. 2 a) thus represents a typical screening situation.

In the case of an undefined outcome of the screening performed according to FIG. 2 a), the same piece of equipment can be used for a more accurate determination according to FIG. 2 b). By undefined outcome is meant that the result is within the tolerance interval of a certain concentration limit. By performing another measurement at higher accuracy (smaller tolerance) it is possible to resolve the undefined situation. In this mode of operation, tight connection between the test subject's respiratory organs and the sensing unit 2 is secured e.g. by applying a tubular receptor 4b, and the test person is instructed to provide forced and prolonged expiration through it, in order to ensure proper emptying of the expiratory air. Since the receptor 5 is tightly fitting to the test person's mouth opening, no dilution of the sample takes place, and correction with $CO_2$ is unnecessary. A prolonged expiration is however required to ensure minimum influence from the physiological dead-space on the measuring result.

Figure 3:
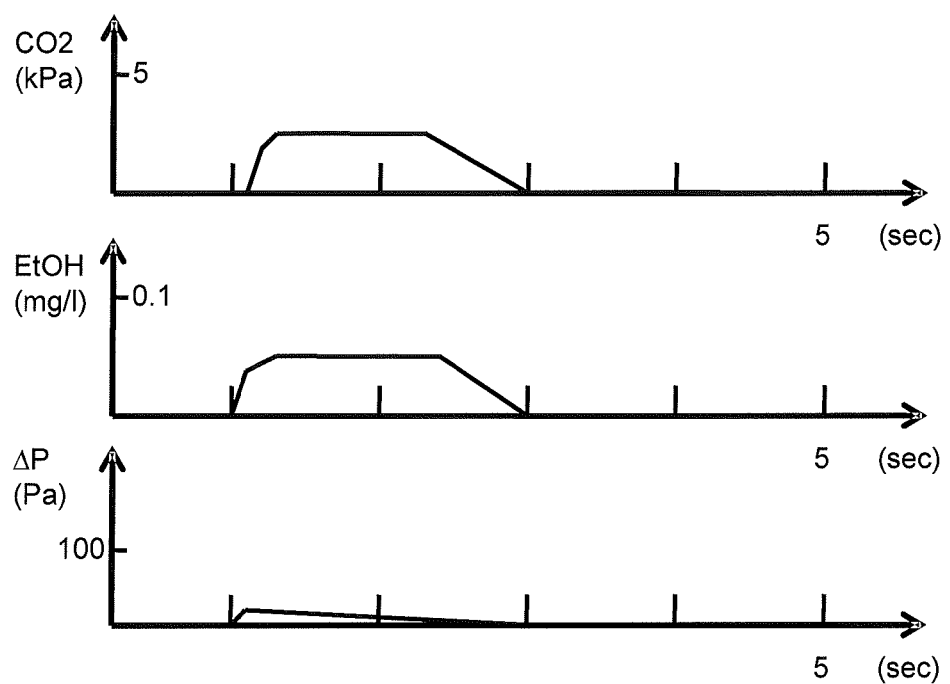
FIG. 3 shows typical signal patterns.
Figure 3:
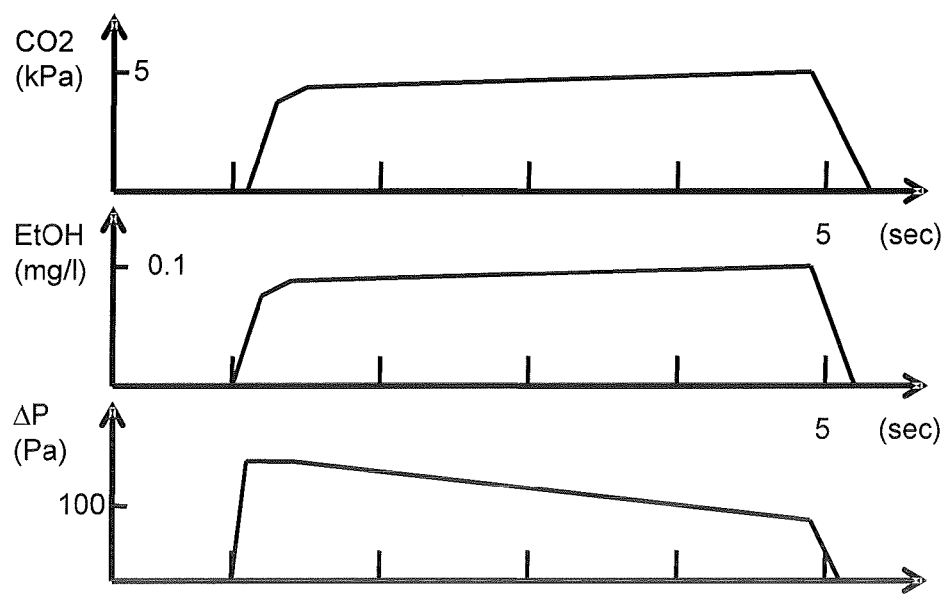

FIG. 3 schematically shows the signal patterns when performing breath tests according to the procedures described above, in relation to FIGS. 2 a) and b). For the screening case FIG. 3 a) graphically shows the variation of the measured concentration of $CO_2$ and the substance of primary interest, in this case ethanol (EtOH) as a function of time during a breath test. A third graph represents the pressure measured at the inlet of the sensing unit 2 by the sensor 16.

All three signals in FIG. 3 a) are basically zero at start, and grow to a maximum during the expiratory phase, and then return to zero as the sensing unit is ventilated. When the $CO_2$ concentration reaches its maximum, the algorithm will assume a dilution ratio of $CO_{2alv}/CO_{2meas}$, and multiply it with the measured ethanol concentration at that time in order to obtain the estimated undiluted EtOH concentration.

The entire course of FIG. 3 a) has a duration of only a few seconds, which is due to the fact that the test person is instructed to terminate the expiration when a certain threshold value of $CO_2$ has been reached, typically 2 kPa, corresponding to a dilution ratio of approximately 2.4.

The pressure signal from the sensor 16 exhibits a minor peak coinciding with the maximum flow. Its magnitude is typically less than 10 Pa ($N/m^2$).

FIG. 3 b) shows the corresponding signal pattern with a tight-fitting receptor 4b. The $CO_2$ concentration is increasing fast in the beginning and is then leveling out. When it exceeds a certain value, e.g. the normal alveolar concentration, the sample may be considered undiluted. The duration is longer in this case than in FIG. 3 a), typically 5 seconds.

The concentration of ethanol follows the same pattern as $CO_2$ with minor deviation, such as an earlier up-rise, and a flatter plateau.

The pressure signal in FIG. 3 b) exhibits a considerably higher peak value than in FIG. 3 a). This is due to the fact that the respiratory organs of the test person generate a significant driving force, especially in the initial phase. The magnitude recorded by the pressure sensor 16 is also depending on the flow resistance of the particle filter 12. The $CO_2$ or the pressure signal is used to determine whether the sample is considered diluted or undiluted. If the pressure in the initial phase exceeds a certain threshold, e.g. 100 Pa, then the connection between the test subject and the sensing unit 2 is considered tight. Then the $CO_{2alv}/CO_{2meas}$ ratio is automatically omitted from the calculation of the substance concentration.

Figure 4:
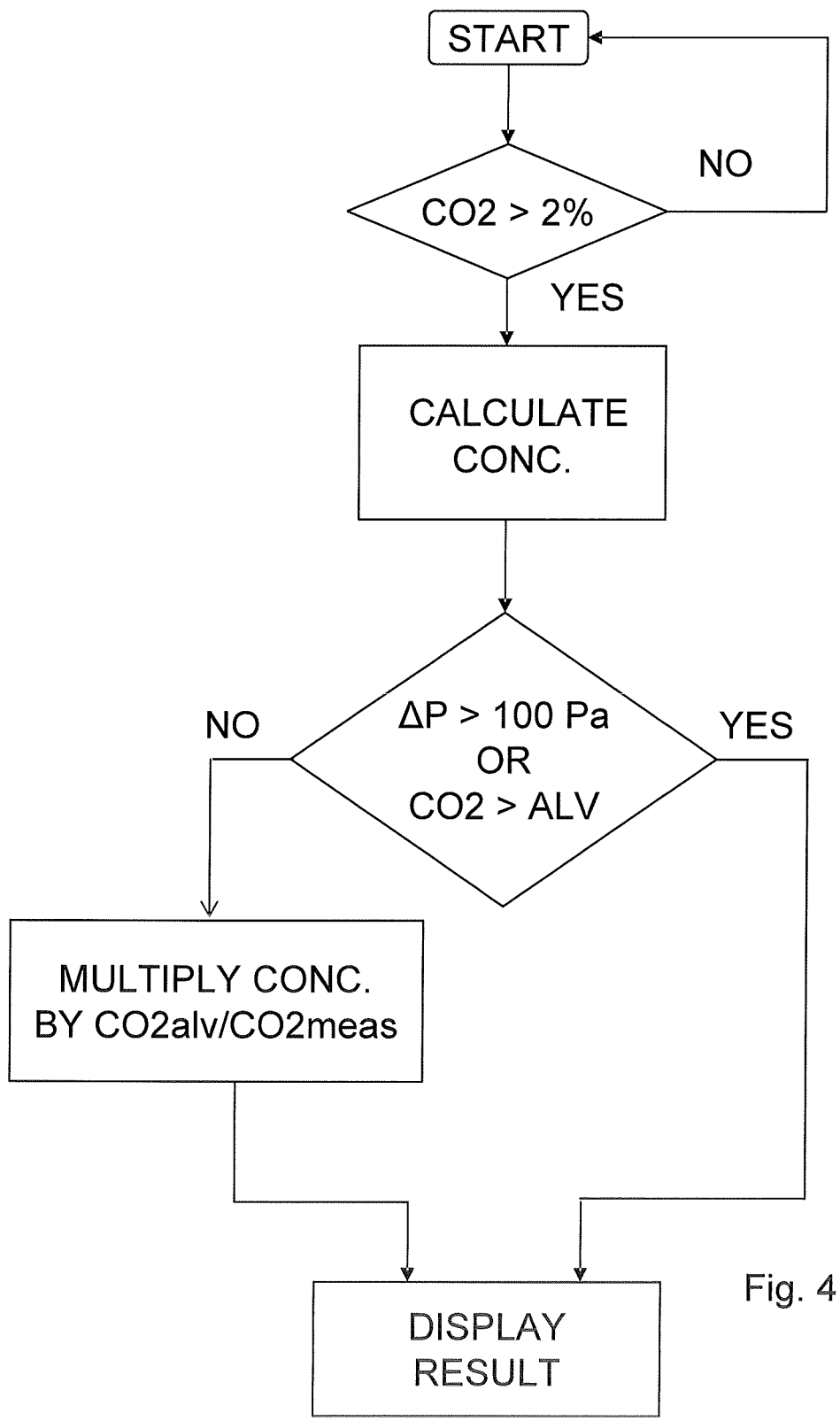
FIG. 4 is a flow chart illustrating the calculations.

A flow chart of the calculations is shown in FIG. 4. The calculation process for obtaining a concentration value for the substance of interest, e.g. ethanol, is initiated when a threshold of measured $CO_2$ concentration is exceeded, e.g. 2% (v/v). Then, if the peak differential pressure of the pressure sensor 16 does not exceed its threshold, e.g. 100 Pa, or if the $CO_2$ concentration does not exceed the alveolar concentration, then the measured substance concentration is multiplied by $CO_{2alv}/CO_{2meas}$, to obtain the estimated concentration which is displayed. If the pressure peak exceeds 100 Pa, or the $CO_2$ signal exceeds the alveolar concentration, then multiplication by $CO_{2alv}/CO_{2meas}$ is omitted.

The invention claimed is:

1. A dual mode breath analyzer, comprising:
   an enclosure (1);
   a receptor unit (4) for receiving a breath sample from a test subject, the receptor unit including a first receptor unit (4a) having the shape of a funnel (4a), scoop, cup or mug for receiving the breath sample from the test subject with the dual mode breath analyzer operating in a contactless mode, and a second receptor unit (4b) having a tubular shape for receiving the breath sample from the test subject with the dual mode breath analyzer operating in a contact mode,
   each of the first receptor unit and the second receptor unit being detachably securable to the enclosure (1) with the first receptor unit being detachably secured to the enclosure for the dual mode breath analyzer operating in the contactless mode and the second receptor unit being detachably secured to the enclosure for the dual mode breath analyzer operating in the contact mode, the contactless mode being a screening operational mode and the contact mode being an operational mode with a higher accuracy than the screening operational mode,
   each of the first and second receptor units having a breath sample inlet and a breath sample outlet;
   a sensing unit (2) located within the enclosure (1) and having an inlet connecting to i) the breath sample outlet of the first receptor unit when the first receptor unit is detachably secured to the enclosure and ii) the breath sample outlet of the second receptor unit when the second receptor unit is detachably secured to the enclosure, the inlet of the sensing unit (2) accepting the breath sample and providing a signal corresponding to a concentration of at least one volatile substance within said sample, said sensing unit (2) including
   a sensor (9) providing a signal corresponding to the concentration of the at least one volatile substance within said sample, and at least one of the group consisting of
a) a differential pressure sensor (16) for providing a dilution signal corresponding to the differential pressure exceeding a preset threshold, over a filter (12) exhibiting a flow resistance included within said sensing unit (2), said dilution signal indicating whether the sample is diluted or undiluted, and
b) a sensor element (8) responsive to $CO_2$ or water vapour to provide a non-dilution signal providing a dilution signal indicating whether the sample is diluted or undiluted;
a signal processing unit (3) configured to analyze said volatile substance to identify and quantify said volatile substance in said breath sample based on both said signal corresponding to the concentration and said dilution signal indicative of the dilution,
wherein said signal processing unit (3) is configured to perform at least two different calculations for the quantification, a first calculation for the screening operational mode and a second calculation for the operational mode with a higher accuracy than the screening operational mode,
wherein said signal processing unit (3) is configured to automatically display a result of a selected calculation, the selection being based on a result of said signal indicating the dilution of said sample by any in the group consisting of i) said threshold of differential pressure being exceeded or not, and ii) the $CO_2$ signal exceeding a normal alveolar concentration or not, and
wherein the dilution signal enables the breath analyzer to be automatically switched, in response to said dilution signal indicating the dilution of said sample, between i) the screening operational mode where said signal processing unit (3) performs the first calculation for the screening operational mode and ii) the operational mode where said signal processing unit (3) performs the second calculation, using a result of the first calculation, with the higher accuracy than the screening operational mode.

2. The breath analyzer according to claim 1, wherein, the sensor is further responsive to a tracer substance within said sample, and said calculation includes a degree of the dilution estimated by simultaneous determination of a concentration of the tracer substance within said sample.

3. The breath analyzer according to claim 1, wherein said at least one volatile substance is ethanol or methanol, acetone, carbon monoxide, carbon dioxide, ammonia, nitric oxides, and tracer substance as marker to distinguish between said breath and ambient air.

4. The breath analyzer according to claim 1, further comprising elements (12, 16) providing a signal indicative of tightness of connection between respiratory organs of said subject and said sensing unit (2), said elements (12, 16) including a well defined flow resistance (12) and a differential pressure sensor (16) having openings (16', 16") upstream and downstream of said flow resistance (12), said openings being directed perpendicular to a main flow direction of said sample.

5. The breath analyzer according to claim 1, wherein said sensing unit (2) includes a geometrically well defined measuring volume, the inlet (5) of which includes the connection to said receptor unit (4a, 4b), and a particle filter (12) for separation of liquid droplets and solid particles within said sample, an outlet of which is connected to ambient air, said measuring volume being smaller than 100 ml, said sensing unit (2) having small but distinctive resistance to air flow, said flow being controllable by a pump, a fan or a valve (10, 11).

6. The breath analyzer according to claim 1, wherein said sensing unit (2) generates a repetitive signal at a repetition frequency of 5 Hz or more, said repetitive signal corresponding to the concentration of said at least one volatile substance within a geometrically defined measuring volume.

7. The breath analyzer according to claim 1, wherein said sensing and signal processing units (2, 3) are based on catalytic measuring principle or based on transmission measurement of multiply reflected electromagnetic radiation against a surface with high reflectance within a defined measuring volume, whereby said analysis includes absorption within a defined wavelength interval for the determination of said at least one volatile substance, and for the determination of a tracer substance.

8. The breath analyzer according to claim 1, wherein said analyzer is contained within an enclosure (1) resistant to environmental stress, and including said sensing and analyzing units, a battery (13) for power source, a display (14) for indication of analysis results, a memory unit for storage of data, switches for data input, and means for data communication (15) to external equipment, said enclosure comprising an autonomous unit for sampling and immediate analysis.

9. The breath analyzer according to claim 1, wherein said enclosure (1) is resistant to environmental stress, and including said sensing and analyzing units, and said analyzer further includes a battery (13) for a power source, a display (14) for indication of analysis results, a memory unit for storage of data, switches for data input, and a dedicated connector for data communication (15) to external equipment, said enclosure comprising an autonomous unit for sampling and immediate analysis.

10. The breath analyzer according to claim 2, wherein the tracer substance to which the sensor is responsive is carbon dioxide or water vapor.

11. The breath analyzer according to claim 3, wherein the tracer substance to which the sensor is responsive is carbon dioxide or water vapor.

12. The breath analyzer according to claim 1, wherein said sensing and signal processing units (2, 3) are based on a catalytic measuring principle sensing said at least one volatile substance as ethyl alcohol, and determining a tracer substance as carbon dioxide.

13. The breath analyzer according to claim 1, wherein said sensing and signal processing units (2, 3) are based on transmission measurement of multiply reflected electromagnetic radiation against a surface with high reflectance within a defined measuring volume, whereby said analysis includes absorption within a defined wavelength interval of 9-10 um for the determination of said at least one volatile substance including ethyl alcohol, and another interval of 4.2-4.3 um for the determination of a tracer substance including carbon dioxide.

14. The breath analyzer according to claim 1, further comprising a fan that draws the breath sample into the inlet of the sensing unit.

15. A dual mode breath analyzer, comprising:
a hand-held enclosure (1);
a battery power source;
switches for data input;
a sensing unit (2) included within the enclosure, the sensing unit (2) including an inlet (5) that accepts a breath sample, the sensing unit providing a signal corresponding to a concentration of a volatile substance within the breath sample, the sensing unit (2) including
a sensor (9) providing a signal corresponding to the concentration of the volatile substance within said sample, and
at least one of the group consisting of
a) a differential pressure sensor (16) for providing a dilution signal corresponding to the differential pressure exceeding a preset threshold, over a filter (12) exhibiting a flow resistance included within said sensing unit (2), said dilution signal indicating whether the sample is diluted or undiluted, an absence of the dilution signal indicating a non-dilution of the breath sample, and
b) a sensor element (8) responsive to $CO_2$ or water vapour to provide a dilution signal indicating whether the sample is diluted or undiluted;
a signal processing unit (3) located within the enclosure and coupled to the sensing unit, the signal processing unit configured to identify and quantify the volatile substance in the breath sample based on both i) said signal corresponding to the concentration of the volatile substance within the breath sample and ii) said signal indicative of the dilution of the volatile substance within the breath sample; and
a receptor unit that secures to the inlet (5) of sensing unit, the receptor unit for receiving the breath sample from a test subject, a first receptor unit including a contactless-mode receptor unit having a shape of a funnel (4a), scoop, cup or mug for contactlessly receiving the breath sample from the test subject in a contactless mode of the breath analyzer, and a second receptor unit (4b) having a tubular shape that receives the breath sample from the test subject in a contact mode of the breath analyzer,
wherein said dual mode breath analyzer is an autonomous unit for sampling and immediate analysis of said breath sample,
wherein the breath analyzer is further configured so that the dilution signal enables the breath analyzer to automatically switch from screening operational mode having the first receptor unit to the operational mode having the second receptor unit with the higher accuracy than the screening operational mode in response to said dilution signal indicating the dilution of said sample, and said signal processing unit (3) is configured to perform at least two different calculations for the quantification, a first calculation for the screening operational mode and a further second calculation, using a result of the first calculation, for the operational mode with the higher accuracy than the screening operational mode.

16. The breath analyzer according to claim 15, further comprising a fan within the sensing unit that draws the breath sample into the inlet of the sensing unit.

17. The dual mode breath analyzer according to claim 1, wherein the preset pressure threshold for the differential pressure sensor is 100 Pa.

18. The dual mode breath analyzer according to claim 1, further comprising a source (7) of electromagnetic radiation within the infrared (IR) wavelength range, and wherein the sensor element responsive to $CO_2$ or water vapour includes IR detectors equipped with band pass interference filters tuned to wavelength intervals which coincide with absorption peaks of the substances to be determined.

19. The dual mode breath analyzer according to claim 1, further comprising a source (7) of electromagnetic radiation within the infrared (IR) wavelength range, and wherein,
the sensor providing a signal corresponding to the concentration of the at least one volatile substance and the sensor element responsive to $CO_2$ are comprised of a first IR detector equipped with band pass interference filter tuned to a wavelength interval which coincide with an absorption peak of the at least one volatile substance, and a second IR detector equipped with band pass interference filter tuned to a wavelength interval which coincide with an absorption peak of $CO_2$.

20. A dual mode breath analyzer comprising:
a receptor unit (4) for receiving a breath sample from a test subject, the receptor unit including a first receptor unit (4a) having the shape of a funnel (4a) scoop, cup or mug for receiving the breath sample from the test subject in a contactless mode of said dual mode breath analyzer, and a second receptor unit (4b) having a tubular shape for receiving the breath sample from the test subject in a contact mode of said dual mode breath analyzer, the contactless mode being a screening operational mode and the contact mode being an operational mode with a higher accuracy than the screening operational mode;
a sensing unit (2) having an inlet for accepting the breath sample, via a filter (12), from i) the first receptor unit (4a) when in the contactless mode of said dual mode breath analyzer, and ii) the second receptor unit (4b) when in the contact mode of said dual mode breath analyzer, said sensing unit (2) including
a) a differential pressure sensor (16) for providing a dilution signal corresponding to a differential pressure across the filter (12) exceeding a preset threshold, the differential pressure across the filter (12) measuring a flow resistance, said dilution signal indicating whether the sample is diluted or undiluted,
b) a sensor element (9) responsive to $CO_2$ concentration and arranged to provide a signal indicating the sample is undiluted when the $CO_2$ concentration exceeds a normal alveolar concentration, and
c) a sensor (8) providing a signal corresponding to a concentration of a volatile substance within said sample and indicating whether the sample is diluted or undiluted;
a signal processing unit (3) configured to analyze said volatile substance to identify and quantify said volatile substance in said breath sample based on both said signal corresponding to the concentration of the volatile substance and said dilution signal indicative of the dilution,
wherein said signal processing unit (3) is configured to perform at least two different calculations for the quantification, a first calculation for the screening operational mode and a second calculation for the operational mode with a higher accuracy than the screening operational mode,
wherein said signal processing unit (3) is configured to automatically display a result of a selected calculation, the selection being based on a result of said signal indicating the dilution of said sample based on i) whether or not said threshold of differential pressure is exceeded, and ii) whether or not the CO2 signal exceeds the normal alveolar concentration; and
wherein the dilution signal enables the breath analyzer to be automatically switched from the screening operational mode to the operational mode, using a result of the first calculation, with the higher accuracy than the screening operational mode in response to said dilution signal indicating the dilution of said sample.

* * * * *